United States Patent
Weiler et al.

(10) Patent No.: US 10,709,683 B2
(45) Date of Patent: *Jul. 14, 2020

(54) LIQUID PHARMACEUTICAL COMPOSITIONS COMPRISING SGLT-2 INHIBITORS

(71) Applicant: Boehringer Ingelheim Vetmedica GmbH, Ingelheim am Rhein (DE)

(72) Inventors: Claudius Weiler, Ingelheim am Rhein (DE); Thomas Duch, Gau-Algesheim (DE); Marbod Haase, Bingen am Rhein (DE); Timothy Shane Priddy, St. Joseph, MO (US); Heike Stettler, Geisenheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/238,346

(22) Filed: Jan. 2, 2019

(65) Prior Publication Data
US 2019/0142787 A1 May 16, 2019

Related U.S. Application Data

(63) Continuation of application No. 15/245,448, filed on Aug. 24, 2016, now Pat. No. 10,220,017.

(30) Foreign Application Priority Data

Aug. 27, 2015 (EP) .................................... 15182715

(51) Int. Cl.
| | | |
|---|---|---|
| A61K 31/351 | (2006.01) | |
| A61K 9/08 | (2006.01) | |
| A61K 47/10 | (2017.01) | |
| A61K 9/00 | (2006.01) | |

(52) U.S. Cl.
CPC .......... *A61K 31/351* (2013.01); *A61K 9/0095* (2013.01); *A61K 9/08* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 7,371,732 B2 | 5/2008 | Eickelmann et al. | |
| 7,375,090 B2 | 5/2008 | Himmelsbach et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,524,822 B2 | 4/2009 | Kraemer et al. | |
| 7,579,449 B2 | 8/2009 | Eckhardt et al. | |
| 7,589,193 B2 | 9/2009 | Washburn et al. | |
| 7,683,160 B2 | 3/2010 | Eckhardt et al. | |
| 7,687,469 B2 | 3/2010 | Eckhardt et al. | |
| 7,713,938 B2 | 5/2010 | Himmelsbach et al. | |
| 7,723,309 B2 | 5/2010 | Himmelsbach et al. | |
| 7,745,414 B2 | 6/2010 | Eckhardt et al. | |
| 7,772,191 B2 | 8/2010 | Eckhardt et al. | |
| 7,772,378 B2 | 8/2010 | Himmelsbach et al. | |
| 7,776,830 B2 | 8/2010 | Eckhardt et al. | |
| 7,847,074 B2 | 12/2010 | Eckhardt et al. | |
| 7,851,502 B2 | 12/2010 | Bindra et al. | |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 7,879,807 B2 | 2/2011 | Himmelsbach et al. | |
| 8,039,441 B2 | 10/2011 | Himmelsbach et al. | |
| 8,080,580 B2 | 12/2011 | Mascitti et al. | |
| 8,283,326 B2 | 10/2012 | Eckhardt et al. | |
| 8,283,454 B2 | 10/2012 | Liou et al. | |
| 8,507,450 B2 | 8/2013 | Eckhardt et al. | |
| 8,551,957 B2 | 10/2013 | Dugi et al. | |
| 8,987,323 B2 | 3/2015 | Cai et al. | |
| 9,145,434 B2 | 9/2015 | Eckhardt et al. | |
| 2003/0064935 A1 | 4/2003 | Gougoutas | |

(Continued)

FOREIGN PATENT DOCUMENTS

| | | |
|---|---|---|
| WO | 0127128 A1 | 4/2001 |
| WO | 2004063209 A2 | 7/2004 |

(Continued)

OTHER PUBLICATIONS

Deshpande et al., "A Practical Stereoselective Synthesis and Novel Cocrystallizations of an Amphiphatic SGLT-2 Inhibitor". Organic Process Research & Development, vol. 16, 2012, pp. 577-585.

(Continued)

*Primary Examiner* — Dale R Miller

(57) ABSTRACT

The invention relates to novel liquid pharmaceutical compositions comprising at least one SGLT-2 inhibitor and one or more polar organic solvents, wherein the at least one SGLT-2 inhibitor comprises 1-cyano-2-(4-cyclopropyl-benzyl)-4-(β-D-glucopyranos-1-yl)-benzene according to formula (I):

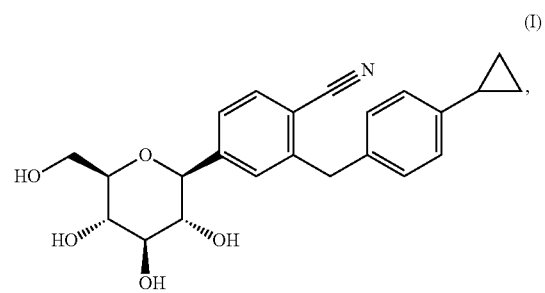

as well as corresponding processes of manufacturing such liquid pharmaceutical compositions and their medical uses.

28 Claims, 1 Drawing Sheet

(56) References Cited

U.S. PATENT DOCUMENTS

| | | |
|---|---|---|
| 2007/0259821 A1 | 11/2007 | Eckhardt et al. |
| 2009/0143316 A1 | 6/2009 | Imamura et al. |
| 2010/0167988 A1 | 7/2010 | Gant et al. |
| 2010/0167989 A1 | 7/2010 | Gant et al. |
| 2010/0249392 A1 | 9/2010 | Eckhardt et al. |
| 2012/0237593 A1 | 3/2012 | Comiskey et al. |
| 2012/0277175 A1 | 7/2012 | Neto et al. |
| 2014/0031540 A1 | 1/2014 | Eckhardt et al. |
| 2014/0303096 A1 | 4/2014 | Iche et al. |
| 2015/0164856 A1 | 6/2015 | Reiche et al. |

FOREIGN PATENT DOCUMENTS

| | | |
|---|---|---|
| WO | 2007093610 A1 | 8/2007 |
| WO | 2007128749 A1 | 11/2007 |
| WO | 2008042688 A2 | 4/2008 |
| WO | 2008116179 A1 | 9/2008 |
| WO | 2009143020 A1 | 11/2009 |
| WO | 2010022313 A2 | 2/2010 |
| WO | 2010023594 A1 | 3/2010 |
| WO | 2010048358 A2 | 4/2010 |
| WO | 2010092125 A1 | 8/2010 |
| WO | 2011153712 | 12/2011 |
| WO | 2012062698 A1 | 5/2012 |
| WO | 2014016381 A1 | 1/2014 |
| WO | 2014161836 | 4/2014 |
| WO | 2015110402 A1 | 7/2015 |
| WO | 2017032799 A1 | 3/2017 |

OTHER PUBLICATIONS

International Search Report and Written Opinion for PCT/EP2016/069977 dated Oct. 7, 2016.

Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes". Journal of Medicinal Chemistry, vol. 57, 2014, pp. 1236-1251.

Chapter 3. Vse o židkostâh [Everything about liquids]. (Aug. 14, 2012).

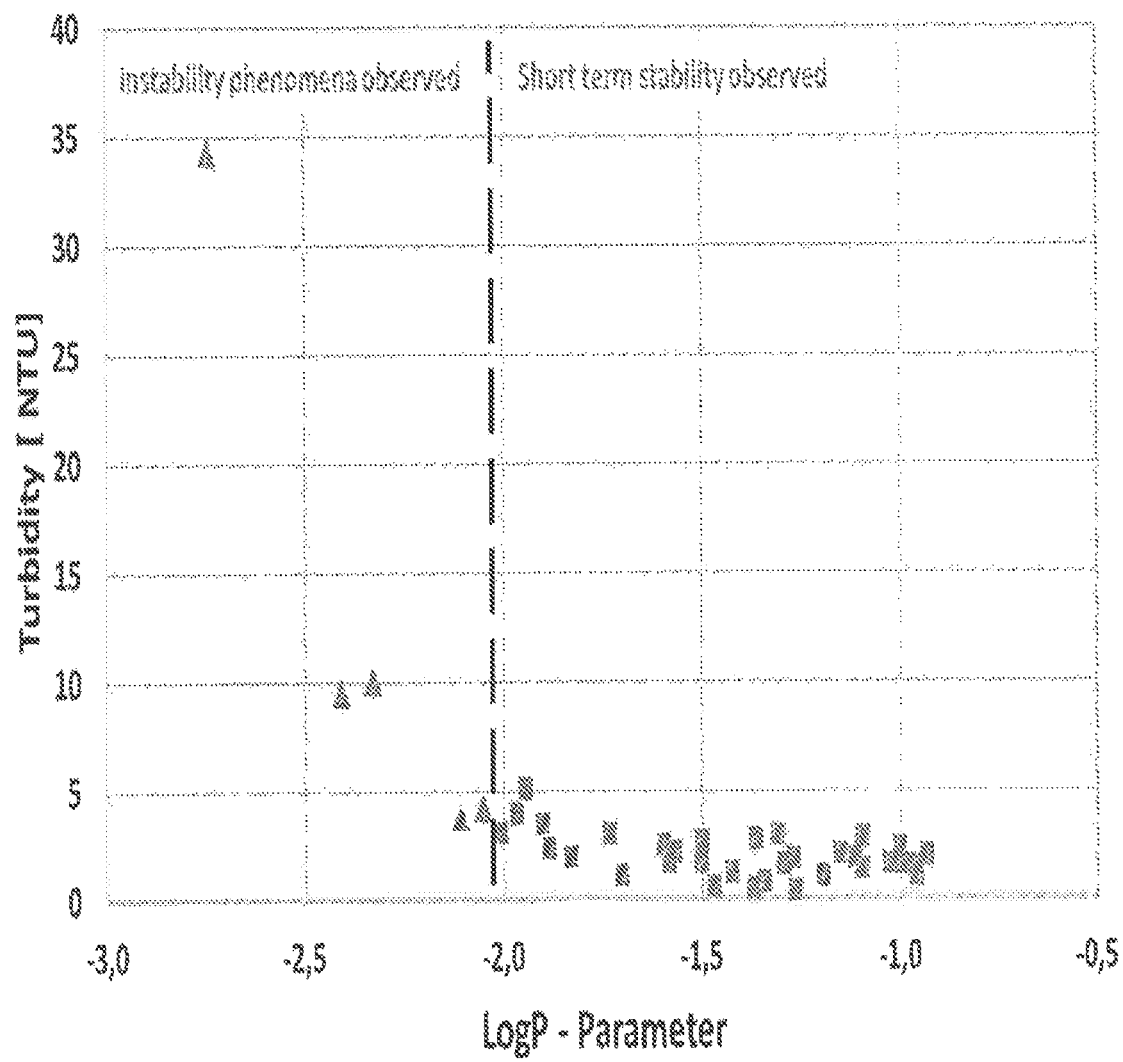

LIQUID PHARMACEUTICAL COMPOSITIONS COMPRISING SGLT-2 INHIBITORS

FIELD OF THE INVENTION

The invention relates to the field of medicine, particularly veterinary medicine. In particular, the invention relates to novel pharmaceutical compositions comprising at least one SGLT-2 inhibitor.

BACKGROUND OF THE INVENTION

The treatment of diabetes and other metabolic disorders includes the inhibition of the renal sodium-dependent glucose co-transporter SGLT-2. SGLT-2 in the kidney regulates glucose levels by mediating the reabsorption of glucose back into the plasma following filtration of the blood. SGLT-2 inhibition thus induces glucosuria and may reduce blood glucose levels.

A large variety of SGLT-2 inhibitors are known. A pharmaceutical formulation of SGLT-2 inhibitors is essential in order to administer such compounds in an adequate way to the patient.

SGLT-2 inhibitors are for instance described in WO 2007/028814 which is directed to crystalline forms of 1-chloro-4-([beta]-D-glucopyranos-1-yl)-2-(4-ethynyl-benzyl)-benzene, a method for the preparation thereof, as well as the use thereof for preparing medicaments. It discloses solutions of 1-chloro-4-([beta]-D-glucopyranos-1-yl)-2-(4-ethynyl-benzyl)-benzene in a solvent or a mixture of solvents and further specifies exemplarily suitable organic solvents such as ethanol or ethanol/water mixtures.

WO 2007/080170 describes crystalline forms of 1'-(1-methylethyl)-4'-[(2-fluoro-4-methoxyphenyl) methyl]-5'-methyl-1H-pyrazol-3'-O-[beta]-D-glucopyranoside, a method for the preparation thereof, as well as the use thereof for preparing medicaments. It discloses solutions of 1'-(1-methylethyl)-4'-[(2-fluoro-4-methoxyphenyl) methyl]-5'-methyl-1H-pyrazol-3'-O-[beta]-D-glucopyranoside in a solvent or a mixture of solvents and further specifies exemplarily suitable organic solvents such as ethanol or ethanol/water mixtures.

In addition, WO 2007/093610 describes glucopyranosyl-substituted benzonitrile derivatives, pharmaceutical compositions containing such compounds, their medical uses as well as processes for their manufacture. It mentions that such glucopyranosyl-substituted benzonitrile derivatives can be formulated among other with one or more inert carriers and/or diluents, such as water/ethanol, water/glycerol, propylene glycol and the like. It further discloses among many other compounds also 1-cyano-2-(4-cyclopropyl-benzyl)-4-(β-D-glucopyranos-1-yl)-benzene.

Further SGLT-2 inhibitors are described in WO 2007/128749 which relates to glucopyranosyl-substituted benzonitrile derivatives, pharmaceutical compositions containing such compounds, their medical uses as well as processes for their manufacture. It mentions that such glucopyranosyl-substituted benzonitrile derivatives can be formulated among other with one or more inert carriers and/or diluents, such as water/ethanol, water/glycerol, propylene glycol and the like. It further discloses among many other compounds also 1-cyano-2-(4-cyclopropyl-benzyl)-4-(β-D-glucopyranos-1-yl)-benzene.

WO 2008/144316 describes crystal structures of a specific glucopyranosyl-substituted benzene derivative being an H-1 form, H-2 form or the (S)-propylene glycol form. It discloses solutions of such specific glucopyranosyl-substituted benzene derivative in water-miscible organic solvents.

Another prior art document WO 2013/079501 is directed to crystalline dapagliflozin hydrate and a method for the preparation thereof. It discloses solutions of dapagliflozin in a solvent or a mixture of solvents and further specifies exemplarily suitable solvents such as water and C1-C4 alcohols or mixtures thereof.

WO 2014/016381 (US 2014/031540) describes crystalline complexes of 1-cyano-2-(4-cyclopropyl-benzyl)-4-(β-D-glucopyranos-1-yl)-benzene with natural amino acids, methods for the preparation thereof as well as the use thereof for preparing medicaments. It discloses solutions of 1-cyano-2-(4-cyclopropyl-benzyl)-4-(β-D-glucopyranos-1-yl)-benzene in a solvent or a mixture of solvents and further specifies exemplarily suitable organic solvents such as C1-C4 alkanols, ethanol and mixtures thereof, in particular with water.

Furthermore, WO 2014/195966 describes amorphous forms of canagliflozin and processes of manufacturing thereof as well as corresponding pharmaceutical compositions and their medicinal uses. It discloses solutions of canagliflozin in one or more organic solvents and further specifies exemplarily suitable organic solvents such as ethanol.

Further challenges known in the prior art are the limited solubility of SGLT-2 inhibitors in water due to their positive $\log_{10} P$ values, which typically influences the bioavailability in the body of a patient or makes it difficult to find adequate solvents to get the substance dissolved in an liquid formulation before administering it into the body of a patient.

Further prior art is as follows:

Xu G et al. (Journal of Medical Chemistry 2014, 57: 1236-1251) is directed to the design, synthesis and biological evaluation of deuterated C-aryl glycosides as potent and long-acting renal SGLT-2 inhibitors for the treatment of type 2 diabetes.

WO 2015/110402 relates to SGLT-2 inhibitors for use in the treatment and/or prevention of metabolic disorders in canine animals.

There is an urgent need for a directly administrable pharmaceutical composition comprising at least one SGLT-2 inhibitor which overcomes the problems of the prior art as described above.

SUMMARY OF THE INVENTION

The present invention concerns a liquid pharmaceutical composition comprising at least one SGLT-2 inhibitor and one or more polar organic solvents, wherein the at least one SGLT-2 inhibitor comprises, preferably is, 1-cyano-2-(4-cyclopropyl-benzyl)-4-(β-D-glucopyranos-1-yl)-benzene according to formula (I):

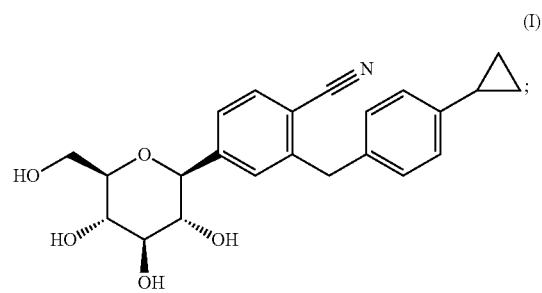 [SMILES: N#Cc1ccc([C@@H]2O[C@H](CO)[C@@H](O)[C@H](O)[C@H]2O)cc1Cc1ccc(C2CC2)cc1]

wherein more preferably 1-cyano-2-(4-cyclopropyl-benzyl)-4-(β-D-glucopyranos-1-yl)-benzene is the only SGLT-2 inhibitor contained in such liquid pharmaceutical composition.

The present invention also concerns a liquid pharmaceutical composition as described and claimed herein for use in a method for treating and/or preventing one or more medicinal indications in a subject in need of such treatment and/or prevention, preferably an animal, more preferably a mammal, in particular a horse, cat or dog, selected from among the medicinal indications:
(i) a metabolic disorder of an equine animal, wherein preferably the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, wherein preferably the metabolic disorder is insulin resistance, hyperinsulinemia, and/or a clinical condition associated with insulin resistance and/or hyperinsulinaemia; wherein preferably said clinical condition is one or more conditions selected from impaired glucose tolerance, dyslipidemia, dysadipokinemia, subclinical inflammation, systemic inflammation, low grade systemic inflammation, obesity, and/or regional adiposity;
(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, wherein preferably the metabolic disorder is a clinical condition/sign associated with insulin resistance and/or hyperinsulinaemia, wherein said clinical condition/sign preferably is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;
(iii) a metabolic disorder of a feline animal, wherein preferably the metabolic disorder is one or more selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained;
(iv) a metabolic disorder of a canine animal, wherein preferably the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or musculoskeletal disorders, and/or Syndrome X (metabolic syndrome), preferably pre-diabetes, insulin dependent diabetes mellitus, insulin resistance diabetes, insulin resistance, wherein preferably the development of hyperglycemia induced cataract formation is prevented or remission is achieved and/or wherein preferably the development of metabolic disorder consequences, such as hypertension, renal dysfunction and/or musculoskeletal disorders, is prevented or progression is slowed or remission is achieved.

The present invention further concerns a process for producing the liquid pharmaceutical composition as described and claimed herein, comprising the steps:
(i) mixing the one or more polar organic solvents;
(ii) optionally, adding water to the mixture resulting from step (i);
(iii) dissolving 1-cyano-2-(4-cyclopropyl-benzyl)-4-(β-D-glucopyranos-1-yl)-benzene in the mixture resulting from step (i) or optionally step (ii);
(iv) optionally, dissolving further excipients, such as pH modifier(s), flavor(s), sweeteners, solubilizing agents, viscosity-enhancing agents and the like, in the mixture resulting from step (iii);
(v) optionally, filtrating the mixture resulting from step (iii) or optionally step (iv);
whereby, optionally, independently from each other after any of the individual process steps—be they mandatory or optional—an additional mixing step is performed.

In the course of the present invention, such process steps (i) to (v) do not need to be carried out in the given order, but can also be performed in any other meaningful order, e.g. (ii)+(i)+(iv)+(iii)+(v). It is within the knowledge of the skilled person to vary the order of process steps in order to obtain the desired process result, i.e. the liquid pharmaceutical composition according to the present invention. For instance, if one or more viscosity-enhancing agents are added, it is preferred to heat the mixture up for complete dissolution of the one or more viscosity-enhancing agents. In turn such resulting mixture needs to be cooled down before the API 1-cyano-2-(4-cyclopropyl-benzyl)-4-(β-D-glucopyranos-1-yl)-benzene (in the form of its L-proline-water cocrystal) is added in order to avoid unnecessary and unwanted degradation of the substance through such heating steps.

The present invention further concerns a kit-of-parts comprising:
(a) a liquid pharmaceutical composition as described and claimed herein; and
(b) a package leaflet including the information that the liquid pharmaceutical composition is to be used for the prevention and/or treatment of one or more medicinal indications in a subject in need of such prevention and/or treatment, which are selected from among the medicinal indications:
(i) a metabolic disorder of an equine animal, wherein preferably the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, wherein preferably the metabolic disorder is insulin resistance, hyperinsulinemia, and/or a clinical condition associated with insulin resistance and/or hyperinsulinaemia; wherein preferably said clinical condition is one or more conditions selected from impaired glucose tolerance, dyslipidemia, dysadipokinemia, subclinical inflammation, systemic inflammation, low grade systemic inflammation, obesity, and/or regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, wherein preferably the metabolic disorder is a clinical condition/sign associated with insulin resistance and/or hyperinsulinaemia, wherein said clinical condition/sign preferably is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein preferably the metabolic disorder is one or more selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained;

(iv) a metabolic disorder of a canine animal, wherein preferably the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or musculoskeletal disorders, and/or Syndrome X (metabolic syndrome), preferably pre-diabetes, insulin dependent diabetes mellitus, insulin resistance diabetes, insulin resistance, wherein preferably the development of hyperglycemia induced cataract formation is prevented or remission is achieved and/or wherein preferably the development of metabolic disorder consequences, such as hypertension, renal dysfunction and/or musculoskeletal disorders, is prevented or progression is slowed or remission is achieved.

The advantages of the liquid pharmaceutical compositions according to the present invention are as follows:

They are suitable for direct administration to a subject without further mandatory processing and/or purification steps. Preferably they are therefore sterile and comply with GMP manufacturing conditions as well as GCP compliant clinical protocols.

They are stable against undesired contamination by/growth of microorganisms.

Ethanol is not necessarily needed as polar organic solvent or can be significantly reduced to a level which is expected to be accepted by animals.

BRIEF DESCRIPTION OF THE FIGURES

FIG. 1 shows the correlation of Turbidity and the Log P-Parameter (according to Example 1, Eq. 4) of solvent mixtures as depicted in Table 2 used for preparing solutions of 1% (w/w) or 1.5% (w/w) 1-cyano-2-(4-cyclopropyl-benzyl)-4-(β-D-glucopyranos-1-yl)-benzene (the substance).

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In the course of the present invention 1-cyano-2-(4-cyclopropyl-benzyl)-4-(β-D-glucopyranos-1-yl)-benzene is also referred to as "the substance" and is herewith understood to also comprise co-crystal 1-cyano-2-(4-cyclopropyl-benzyl)-4-(β-D-glucopyranos-1-yl)-benzene-L-proline as well as the co-crystal monohydrate 1-cyano-2-(4-cyclopropyl-benzyl)-4-(β-D-glucopyranos-1-yl)-benzene-L-proline-water (as disclosed in WO 2014/016381). Generally, in the case of disclosed and claimed mass concentrations (% w/w) and amounts (g, mg) the mass concentration or amount always refers to the "free base" 1-cyano-2-(4-cyclopropyl-benzyl)-4-(β-D-glucopyranos-1-yl)-benzene-L-proline, i.e. excluding L-proline and crystal water, unless otherwise explicitly stated—even though in practice (and in the example section) co-crystal 1-cyano-2-(4-cyclopropyl-benzyl)-4-(β-D-glucopyranos-1-yl)-benzene-L-proline-water is actually added/used.

In the course of the present invention the term "suitable for direct administration to a subject" in connection with "liquid pharmaceutical composition" means that such liquid pharmaceutical compositions can be directly administration to a subject without further mandatory processing and/or purification steps and explicitly excludes (mixtures of) organic solvents that are solely mentioned in the context of producing crystalline complexes of SGLT2 inhibitors. Preferably, such "liquid pharmaceutical composition" that are "suitable for direct administration to a subject" are therefore sterile and/or comply with GMP manufacturing conditions as well as GCP compliant clinical protocols.

In one aspect, the present invention relates to a liquid pharmaceutical composition as described and claimed herein, wherein the liquid pharmaceutical composition is suitable for direct administration to a subject, preferably an animal, more preferably a mammal, in particular a horse, cat or dog; wherein preferably the liquid pharmaceutical composition is sterile.

In another aspect, the present invention relates to a liquid pharmaceutical composition as described and claimed herein, wherein the liquid pharmaceutical composition is a solution, an emulsion or a suspension, preferably a solution, an emulsion or a suspension with an NTU value of equal to or less than 10.0, more preferably equal to or less than 7.0, even more preferably equal to or less than 3.0, and most preferably a solution, in particular a solution with an NTU value of equal to or less than 3.0.

In the course of the present invention the term "NTU" refers to Nephelometric Turbidity Units and to an opalescent value as defined and described in European Pharmacopoeia 8th edition (Ph. Eur. 8, Chapter 2.2.1. "Clarity and degree of opalescence of liquids").

In another aspect, the present invention relates to a liquid pharmaceutical composition as described and claimed herein, wherein the one or more polar organic solvents are independently from each other characterized by a negative $\log_{10}$ P value, preferably a negative decadic logarithmic partition coefficient (P) in an n-octanol/water system according to formula (II):

$$\log_{10} P_{n\text{-}octanol/water} = \text{concentration of unionized compound in } n\text{-octanol/concentration of unionized compound in water} \quad \text{(II)}$$

In a further aspect, the present invention relates to a liquid pharmaceutical composition as described and claimed herein, wherein such liquid pharmaceutical composition as a whole is characterized by a negative Log P-Parameter, preferably a negative Log P-Parameter of equal to or less than −2.0 (i.e. −2.0≤Log P-Parameter<0). For the avoidance of doubt, the Log P-Parameter is defined as in Eq. 4 of Example 1 and is not identical with and should not be mistaken for the (negative) $\log_{10}$ P value as given for the one or more polar organic solvent(s).

In yet another aspect, the present invention relates to a liquid pharmaceutical composition as described and claimed herein, wherein the one or more polar organic solvents are selected from ethanol ($\log_{10}$ P: −0.16), propane-1,2-diol (propylene glycol; $\log_{10}$ P: −0.79), propane-1,2,3-triol (glycerol; $\log_{10}$ P: −1.84). The $\log_{10}$ P values were taken from http://www.chemicalize.org/.

In yet another aspect, the present invention relates to a liquid pharmaceutical composition as described and claimed herein, wherein such liquid pharmaceutical composition comprises at least two different polar organic solvents, preferably two or three different polar organic solvents, more preferably propane-1,2-diol (propylene glycol) and propane-1,2,3-triol (glycerol) or ethanol and propane-1,2-diol (propylene glycol) or ethanol and propane-1,2-diol (propylene glycol) and propane-1,2,3-triol (glycerol). Preferably, if ethanol is present in the liquid pharmaceutical composition as described and claimed herein, it is present at no more than 20 g/100 mL (20% w/w), preferably it is present at no more than 15 g/100 mL (15% w/w), more preferably it is present at no more than 10 g/100 mL (15% w/w), most preferably it is present at 8 g/100 mL (8% w/w).

In yet another aspect, the present invention relates to a liquid pharmaceutical composition as described and claimed herein, wherein such liquid pharmaceutical composition does not comprise ethanol as the one or more polar organic solvents.

In yet another aspect, the present invention relates to a liquid pharmaceutical composition as described and claimed herein, wherein such liquid pharmaceutical composition does not comprise only propane-1,2-diol (propylene glycol) as single polar organic solvent.

In yet another aspect, the present invention relates to a liquid pharmaceutical composition as described and claimed herein, wherein such liquid pharmaceutical composition additionally comprises water, preferably aqueous buffer, such as citric acid buffer (preferably with pH 6.0) or phosphate buffer (preferably with pH 6.8).

In yet another aspect, the present invention relates to a liquid pharmaceutical composition as described and claimed herein, wherein such liquid pharmaceutical composition has a measured pH value of from 3 to 9, preferably from 4 to 9, more preferably from 5.0 to 8.5, even more preferably from 6.0 to 8.5 and most preferably from 6.0 to 7.5. For the avoidance of doubt, the term "measured pH value" refers to the pH value actually measured for the whole liquid pharmaceutical composition according to the present invention, although puristically only pH values of pure aqueous systems can be measured by means of standard pH determination methods.

In yet another aspect, the present invention relates to a liquid pharmaceutical composition as described and claimed herein, wherein such liquid pharmaceutical composition additionally comprises one or more solubilizing agents, preferably selected from the group consisting of: "surfactants, anionic surfactants, non-ionic surfactants, hydrogenated castor oils, polyoxyethylene-polyoxypropylene block copolymers, polyethylene glycols, propylenglycol derivatives", more preferably selected from the group consisting of: "Sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 300, propylenglycol monolaurate" and/or additionally comprises one or more viscosity-enhancing agents, preferably selected from the group consisting of: "inorganic gel forming agents, organic gel forming agents, cellulose derivatives", more preferably selected from the group consisting of: "hydroxyl ethyl cellulose, hydroxyl propyl methyl cellulose, silicon dioxide" and/or additionally comprises one or more flavors and/or sweeteners, preferably selected from the group consisting of: "honey flavor, lime/salvia flavor, jasmine flavor, lavender flavor, peppermint flavor, raspberry flavor, lemon flavor, herbs flavor, saccharine, aspartame".

In yet another aspect, the present invention relates to a liquid pharmaceutical composition as described and claimed herein, wherein such liquid pharmaceutical composition does not comprise any apolar organic solvents, which are preferably and independently from each other characterized by a $\log_{10}$ P value of equal to or higher than 0.

In yet another aspect, the present invention relates to a liquid pharmaceutical composition as described and claimed herein, wherein such liquid pharmaceutical composition is for oral and/or parenteral administration, preferably oral administration.

In yet another aspect, the present invention relates to a liquid pharmaceutical composition as described and claimed herein, comprising
(i) 0.5-5.0 g/100 mL (% w/w), preferably 1.0-1.5 g/100 mL (% w/w) 1-cyano-2-(4-cyclopropyl-benzyl)-4-(β-D-glucopyranos-1-yl)-benzene;
(ii) 10-60 g/100 mL (% w/w), preferably 35-60 g/100 mL (% w/w), more preferably 50-60 g/100 mL (% w/w) propylene glycol;
(iii) 0-60 g/100 mL (% w/w), preferably 0-52 g/100 mL (% w/w) glycerol;
(iv) 0-20 g/100 mL (% w/w), preferably 0-15 g/100 mL (% w/w), more preferably 0-10 g/100 mL (% w/w), most preferably 0-8 g/100 mL (% w/w) ethanol;

(v) 0-1 g/100 mL (% w/w), preferably 0-0.15 g/100 mL (% w/w) flavor and/or sweetener, more preferably selected from the group consisting of "honey flavor, lime/salvia flavor, jasmine flavor, lavender flavor, peppermint flavor, raspberry flavor, lemon flavor, herbs flavor, saccharine, and/or aspartame";

(vi) 0-52 g/100 mL (% w/w), preferably 0-40 g/100 mL (% w/w) aqueous buffer, preferably citric acid buffer pH 6.0 or phosphate buffer pH 6.8;

(vii) 0-10 g/100 mL (% w/w), preferably 0-8 g/100 mL (% w/w) solubilizing agent, preferably selected from the group consisting of: "surfactants, anionic surfactants, non-ionic surfactants, hydrogenated castor oils, polyoxyethylene-polyoxypropylene block copolymers, polyethylene glycols, and/or propylenglycol derivatives", more preferably selected from the group consisting of: "Sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 300, and/or propylenglycol monolaurate";

(viii) 0-5 g/100 mL (% w/w), preferably 0-0.5 g/100 mL (% w/w) viscosity-enhancing agent, preferably selected from the group consisting of "inorganic gel forming agents, organic gel forming agents, and/or cellulose derivatives", more preferably selected from the group consisting of "hydroxyl ethyl cellulose, hydroxyl propyl methyl cellulose, and/or silicon dioxide".

In yet another aspect, the present invention relates to a liquid pharmaceutical composition as described and claimed herein, selected from:

EXAMPLES

The following examples serve to further illustrate the present invention; but the same should not be construed as a limitation of the scope of the invention disclosed herein.

Example 1

The testing criteria applied are those for evaluation of the clarity of a liquid (formulation) comprising 1-cyano-2-(4-cyclopropyl-benzyl)-4-(β-D-glucopyranos-1-yl)-benzene according to Pharm. Eur. 8. Concerning the Ph. Eur. 8, Chapter 2.2.1. "Clarity and degree of opalescence of liquids", a liquid is considered clear if its opalescence is not more pronounced than that of reference suspension I having an opalescent value of 3 NTU (Table 1).

TABLE 1

| Measurements of reference suspensions I-IV according Pharm. Eur. 8, Chapter 2.2.1 ||
| --- | --- |
| Formazin suspensions | Opalescent values (NW) |
| Reference suspension I | 3 |
| Reference suspension II | 6 |
| Reference suspension III | 18 |
| Reference suspension IV | 30 |
| Standard of opalescence | 60 |
| Primary opalescent suspension | 4000 |

In the following Table 2 exemplary pharmaceutical compositions of solvents which were mixed with 1-cyano-2-(4-cyclopropyl-benzyl)-4-(β-D-glucopyranos-1-yl)-benzene (the substance) according to the present invention are given

| Ingredient | Composition 1 [%(w/w)] | Composition 2 [%(w/w)] | Composition 3 [%(w/w)] | Composition 4 [%(w/w)] | Composition 5 [%(w/w)] | Composition 6 [%(w/w)] | Composition 7 [%(w/w)] |
| --- | --- | --- | --- | --- | --- | --- | --- |
| 1-cyano-2-(4-cyclopropyl-benzyl)-4-(β-D-glucopyranos-1-yl)-benzene | 1.5 | 1.5 | 1.5 | 1.5 | 1.5 | 1.5 | 1.0 |
| Propylene glycol | 60 | 60 | 60 | 60 | 60 | 60 | 52 |
| Water | 23.5 | 27.5 | 22.4 | 23.2 | 27.0 | 21.9 | 49.9 |
| Glycerol 85% | 17.6 | 0.0 | 11.8 | 17.6 | 0.0 | 11.8 | — |
| Ethanol, abs. | — | 8 | 5 | — | 8 | 5 | — |
| NaOH, 1N | 4.71 | 5.51 | 4.49 | 4.63 | 5.41 | 4.39 | — |
| Citric acid, monohydrate | 0.36 | 0.42 | 0.34 | 0.35 | 0.41 | 0.33 | — |
| Honey flavor | — | — | — | 0.15 | 0.15 | 0.15 | — |
| Disodium hydrogen phosphate dodecahydrate | — | — | — | — | — | — | 0.890 |
| Potassium hydrogen phosphate | — | — | — | — | — | — | 0.350 | in detail (Gly: glycerol; PG: propylene glycol, EtOH: ethanol). The turbidity was measured by using a Hach Lange 2100 N IS apparatus.

The following procedure was used to prepare the samples:
1. Weigh entire amount of solvents into vessel
2. Weigh entire amount of buffer into the vessel, close the vessel and mix it.
3. Weigh entire amount of 1-cyano-2-(4-cyclopropyl-benzyl)-4-(β-D-glucopyranos-1-yl)-benzene into the vessel, close the vessel and mix it over about 2 minutes.
4. Place the vessel into an ultrasonic bath until the solution is particle free and free of air bubbles.
5. Measure turbidity and pH value $$Mo_i = \frac{mo_i}{\sum_{i=1}^{n} mo_i} \quad \text{(Eq. 1)}$$

$$LogPo = \sum_{i=1}^{n} (Mo_i \cdot LogP_i) \quad \text{(Eq. 2)}$$

$$X_o = 1 - \frac{a_w}{a_{sol}} \quad \text{(Eq. 3)}$$

$$LogP \text{ Parameter} = \frac{LogPo}{X_o} \quad \text{(Eq. 4)}$$

TABLE 2

| V | Gly [%] | PG [%] | EtOH [%] | Buffer [%] | Buffer pH 6.8 | Buffer pH 6.0 | Addition of the substance [% (m/m)] | Turbidity [NTU] | pH | Instability at RT observed | $\log_{10}P$ - Parameter |
|---|---|---|---|---|---|---|---|---|---|---|---|
| 1  | 10.0 | 49.9 | 0.0  | 40.0 | X | — | 1   | 2.2  | 7.6 | —   | −1.6 |
| 2  | 10.1 | 39.9 | 0.0  | 50.0 | X | — | 1   | 5.2  | 7.4 | —   | −1.9 |
| 3  | 30.0 | 40.0 | 0.0  | 30.0 | X | — | 1   | 1.2  | 7.5 | —   | −1.7 |
| 4  | 20.0 | 40.0 | 0.0  | 40.0 | X | — | 1   | 2.0  | 7.4 | —   | −1.8 |
| 5  | 10.1 | 44.9 | 0.0  | 45.0 | X | — | 1   | 3.1  | 7.5 | —   | −1.7 |
| 6  | 35.0 | 30.0 | 0.0  | 35.0 | X | — | 1   | 3.2  | 7.3 | —   | −2.0 |
| 7  | 30.0 | 35.0 | 0.0  | 35.0 | X | — | 1   | 2.4  | 7.3 | —   | −1.9 |
| 8  | 30.0 | 20.0 | 0.0  | 50.0 | X | — | 1   | 34.3 | 7.1 | Yes | −2.7 |
| 9  | 20.0 | 30.0 | 0.0  | 50.0 | X | — | 1   | 10.1 | 7.2 | Yes | −2.3 |
| 10 | 40.0 | 20.0 | 0.0  | 40.0 | X | — | 1   | 9.5  | 7.2 | Yes | −2.4 |
| 11 | 30.0 | 10.0 | 0.0  | 60.0 | X | — | 1   | 3.4  | 7.0 | Yes | −3.8 |
| 12 | 20.1 | 35.0 | 0.0  | 45.0 | X | — | 1   | 4.3  | 7.3 | Yes | −2.1 |
| 13 | 25.0 | 35.0 | 0.0  | 40.0 | X | — | 1   | 4.0  | 7.5 | —   | −2.0 |
| 14 | 30.0 | 30.0 | 0.0  | 40.0 | X | — | 1   | 3.9  | 7.3 | Yes | −2.1 |
| 15 | 25.7 | 36.2 | 0.0  | 38.0 | X | — | 1   | 3.5  | 7.4 | —   | −1.9 |
| 16 | 40.0 | 50.0 | 0.0  | 10.0 | X | — | 1   | 0.9  | 7.9 | —   | −1.3 |
| 17 | 20.0 | 50.0 | 0.0  | 30.0 | X | — | 1   | 2.7  | 7.6 | —   | −1.5 |
| 18 | 25.0 | 45.1 | 0.0  | 29.9 | X | — | 1   | 2.6  | 7.6 | —   | −1.6 |
| 19 | 30.1 | 49.9 | 0.0  | 20.0 | X | — | 1   | 1.3  | 7.7 | —   | −1.4 |
| 20 | 35.0 | 45.0 | 0.0  | 20.0 | X | — | 1   | 1.8  | 7.6 | —   | −1.5 |
| 21 | 40.1 | 40.0 | 0.0  | 20.0 | X | — | 1   | 1.8  | 8.0 | —   | −1.6 |
| 22 | 50.0 | 50.0 | 0.0  | 0.0  | X | — | 1   | 0.5  | 7.8 | —   | −1.3 |
| 23 | 49.9 | 40.1 | 0.0  | 10.0 | X | — | 1   | 0.6  | —   | —   | −1.5 |
| 24 | 59.9 | 40.1 | 0.0  | 0.0  | X | — | 1   | 0.6  | —   | —   | −1.4 |
| 25 | 10.0 | 60.0 | 0.0  | 30.0 | X | — | 1.5 | 3.0  | 7.8 | —   | −1.3 |
| 26 | 19.9 | 60.0 | 0.0  | 20.1 | X | — | 1.5 | 2.0  | 7.9 | —   | −1.3 |
| 27 | 0.0  | 60.0 | 5.0  | 35.0 | X | — | 1.5 | 2.9  | 7.9 | —   | −1.1 |
| 28 | 10.1 | 59.9 | 4.9  | 25.0 | X | — | 1.5 | 2.0  | 7.9 | —   | −1.1 |
| 29 | 20.0 | 59.9 | 5.0  | 15.0 | X | — | 1.5 | 1.5  | 8.1 | —   | −1.1 |
| 30 | 0.0  | 60.0 | 10.0 | 30.0 | X | — | 1.5 | 2.1  | 8.1 | —   | −0.9 |
| 31 | 10.0 | 60.0 | 10.0 | 20.0 | X | — | 1.5 | 1.6  | 8.2 | —   | −1.0 |
| 32 | 20.0 | 60.0 | 10.0 | 10.0 | X | — | 1.5 | 1.1  | 8.4 | —   | −1.0 |
| 33 | 15.0 | 59.9 | 0.0  | 25.0 | X | — | 1.5 | 1.7  | 7.9 | —   | −1.3 |
| 34 | 0.0  | 60.0 | 8.0  | 32.0 | X | — | 1.5 | 1.7  | 8.0 | —   | −1.0 |
| 35 | 15.0 | 60.0 | 2.5  | 22.6 | X | — | 1.5 | 1.2  | 8.0 | —   | −1.2 |
| 36 | 5.0  | 59.9 | 7.5  | 27.6 | X | — | 1.5 | 1.7  | 8.0 | —   | −1.0 |
| 37 | 14.2 | 56.8 | 0.0  | 28.9 | — | X | 1.5 | 2.9  | 7.2 | —   | −1.4 |
| 38 | 0.0  | 59.5 | 7.9  | 32.6 | — | X | 1.5 | 2.4  | 7.3 | —   | −1.0 |
| 39 | 9.7  | 58.1 | 4.8  | 27.4 | — | X | 1.5 | 2.2  | 7.3 | —   | −1.2 |

The mixtures of solvents applied for experiments V8 to V12 and V14 showed instability phenomena like visible sediments in the solution or on the bottom of the vessel within 3 weeks short term storage at room temperature.

In order to quantify the solvent characteristics of these mixtures regarding their suitability to form a physical stable solution with the substance, a Log P-Parameter was introduced (Eq. 4). The Log P-Parameter describes the hydrophilic/hydrophobic nature of solvent mixture containing organic and aqueous solvents and is calculated as follows:

$mo_i$ [mol/g]: molecular amount of an organic solvent in the organic phase of a solvent mixture $Mo_i$ [–]: molecular fraction of organic solvent $mo_i$ in the organic phase of a solvent mixture Log $P_i$ [–]: $\log_{10} P_{n\text{-}octanol/water}$=concentration of unionized compound in n-octanol/concentration of unionized compound in water of an organic solvent Log Po [–]: auxiliary parameter of the organic phase of a solvent mixture $a_w$ [g]: mass of water or aqueous buffer in a solvent mixture $a_{sol}$ [g]: mass of solvent mixture $X_o$ [-]: mass fraction of organic phase in a solvent mixture Exemplary Calculation For glycerol the $\log_{10}$ P value (=Log $P_1$) is given as −1.84 and the molecular weight as 92.09 g/mol. 1 g of solvent mixture of V1 contains 10% glycerol which corresponds to 0.1 g glycerol or 0.001086 mol (=$mo_{glycerol}$). The other organic solvent is propylene glycol (PG) having a $\log_{10}$ P value (=Log $P_i$) of −0.79 and a molecular weight of 76.09 g/mol. 1 g of the solvent mixture of V1 contains 49.9% PG which corresponds to 0.499 g PG or 0.006558 mol (=$mo_{PG}$). Concerning Eq. 1 $Mo_{glycerol}$ is 0.142 and $Mo_{PG}$ is 0.858. Log Po is calculated as −0.94 (Eq. 2). 1 g of solvent mixture of V1 contains 40% aqueous buffer which results in a mass fraction of organic phase of $X_o$=0.6 (Eq. 3). Following Eq. 4 a Log P Parameter of −1.6 is calculated for the solvent mixture of experiment V1. For mixtures containing ethanol, a $\log_{10}$ P value (=Log $P_i$) for ethanol of −0.16 and a molecular weight of 46.07 g/mol was used.

By correlating the measured Turbidity over the values for the Log P-Parameter between −3.0 and −0.5, an exponential function is observed (FIG. 1). Furthermore it was found, that solvent mixtures prepared with the phosphate buffer pH 6.8 or the citric acid buffer pH 6.0 having a Log P-Parameter≥2.1 are physically instable after preparing a solution with the substance.

Example 2

In the following Table 3 exemplary pharmaceutical compositions according to the present invention are given in detail (API: active pharmaceutical ingredient).

TABLE 3

Exemplary pharmaceutical compositions according to the present invention

| Ingredient | Concentration [g/100 mL (% w/w)] | Function |
| --- | --- | --- |
| 1-cyano-2-(4-cyclopropyl-benzyl)-4-(β-D-glucopyranos-1-yl)-benzene | 0.5-5.0; preferably 1.0-1.5 | API |
| Propylene glycol | 10-60, preferably 35-60; more preferably 50-60 | Solvent |
| Glycerol | 0-60; preferably 0-52 | Solvent |
| Ethanol, abs. | 0-20; preferably 0-15; more preferably 0-10; most preferably 0-8 | Solvent |
| Flavor | 0-1; preferably 0-0.15 | Flavor |
| Aqueous buffer (e.g. citric acid buffer pH 6.0 or phosphate buffer pH 6.8) | 0-52; preferably 0-40 | pH adjustment |

The production procedure of an exemplary pharmaceutical composition according to the present invention for a single small scale batch (100 mL) in form of a general instruction is as follows:

Prepare buffer solution

Weigh aqueous buffer solution in a vessel.

Weigh propylene glycol and add to buffer solution under stirring.

Weigh glycerol and add to the solution under stirring.

Weigh ethanol and add to the solution under stirring.

Weigh flavor and add to the solution under stirring.

Weigh 1-cyano-2-(4-cyclopropyl-benzyl)-4-(β-D-glucopyranos-1-yl)-benzene and add in portions to the solution.

Stir until fully dissolved.

Filtration of the solution.

Example 3

Formulation samples were produced with compositions listed in the following Table 4.

TABLE 4

| Ingredient | Composition 1 [g/100 mL] | Composition 2 [g/100 mL] | Composition 3 [g/100 mL] | Composition 4 [g/100 mL] | Composition 5 [g/100 mL] | Composition 6 [g/100 mL] | Composition 7 [g/100 mL] |
| --- | --- | --- | --- | --- | --- | --- | --- |
| 1-cyano-2-(4-cyclopropyl-benzyl)-4-(β-D-glucopyranos-1-yl)-benzene | 1.5 | 1.5 | 1.5 | 1.5 | 1.5 | 1.5 | 1.0 |
| Propylene glycol | 60 | 60 | 60 | 60 | 60 | 60 | 52 |
| Water | 23.5 | 27.5 | 22.4 | 23.2 | 27.0 | 21.9 | 49.9 |
| Glycerol 85% | 17.6 | 0.0 | 11.8 | 17.6 | 0.0 | 11.8 | — |
| Ethanol. abs. | — | 8 | 5 | — | 8 | 5 | — |
| NaOH. 1N | 4.71 | 5.51 | 4.49 | 4.63 | 5.41 | 4.39 | — |
| Citric acid. monohydrate | 0.36 | 0.42 | 0.34 | 0.35 | 0.41 | 0.33 | — |

TABLE 4-continued

| Ingredient | Composition 1 [g/100 mL] | Composition 2 [g/100 mL] | Composition 3 [g/100 mL] | Composition 4 [g/100 mL] | Composition 5 [g/100 mL] | Composition 6 [g/100 mL] | Composition 7 [g/100 mL] |
|---|---|---|---|---|---|---|---|
| Honey flavor | — | — | — | 0.15 | 0.15 | 0.15 | — |
| Disodium hydrogen phosphate dodecahydrate | — | — | — | — | — | — | 0.890 |
| Potassium hydrogen phosphate | — | — | — | — | — | — | 0.350 |

The following procedure was used to prepare the samples:
1. Weigh entire amount of water into vessel
2. Weigh entire amounts of NaOH 1N and citric acid monohydrate or disodium hydrogen phosphate dodecahydrate and potassium hydrogen phosphate into a beaker and add to stirred water. Stir until fully dissolved.
3. Weigh entire amount of propylene glycol into a beaker and add slowly to stirred solution.
4. Weigh entire amount of glycerol 85% into a beaker and add to stirred solution. Stir until fully mixed.
5. Weigh entire amount of ethanol, abs. into a beaker and add to stirred solution. Stir until fully mixed.
6. Weigh entire amount of flavor into a beaker and add to stirred solution. Stir until fully dissolved.
7. Weigh entire amount of 1-cyano-2-(4-cyclopropyl-benzyl)-4-(β-D-glucopyranos-1-yl)-benzene into a beaker and add in portions to stirred solution. Stir until fully dissolved.
8. Use a 8 μm Filter to filtrate the solution The solutions were found to have the following densities and appearances (Table 5).

TABLE 5

| Formulation/ Solution | Turbidity [NTU] | Density [g/mL] | Appearance |
|---|---|---|---|
| Composition 1 | 1.8 | 1.077 | yellowish, clear solution, no particles |
| Composition 2 | 1.6 | 1.029 | yellowish, clear solution, no particles |
| Composition 3 | 1.5 | 1.055 | yellowish, clear solution, no particles |
| Composition 4 | 1.3 | 1.077 | yellowish, clear solution, no particles |
| Composition 5 | 1.1 | 1.028 | yellowish, clear solution, no particles |
| Composition 6 | 1.1 | 1.054 | yellowish, clear solution, no particles |
| Composition 7 | 5.8 | 1.046 | yellowish, clear solution, no particles |

Example 4

The testing criteria applied are those for evaluation of antimicrobial activity for oral preparations according to Pharm. Eur. 7 (tests at 14 days and 28 days). The acceptance criteria of the Ph. Eur. 7, Method 5.1.3 "Efficacy of Antimicrobial Preservation", and USP 34, Method <51> "Antimicrobial Effectiveness Testing" are listed in the following Table 6.

TABLE 6

Criteria for evaluation of antimicrobial activity for oral preparations according to Pharm. Eur. 7 and USP 34

| Type of microorganism | Ph. Eur. 7 Method 5.1.3. | | USP 34 Method <51> | |
|---|---|---|---|---|
| | Logarithmic reduction of microorganisms after | | | |
| | 14 days | 28 days | 14 days | 28 days |
| Bacteria | >3 | No increase from 14 days [1] | >1.0 | No increase from 14 days [2] |
| Fungi | >1 | No increase from 14 days [1] | No increase from initial calc. count [2] | No increase from initial calc. count [2] |

[1] for Ph. Eur: No increase = no increase in number
[2] for USP: No increase = not more than 0.5 $\log_{10}$ units higher than reference value The formulations tested in the trial are shown in the following Table 7.

TABLE 7

| Ingredient | Trial 1 [g/100 mL] | Trial 2 [g/100 mL] | Trial 3 [g/100 mL] | Trial 4 [g/100 mL] | Trial 5 [g/100 mL] | Trial 6 [g/100 mL] |
|---|---|---|---|---|---|---|
| 1-cyano-2-(4-cyclopropyl-benzyl)-4-(β-D-glucopyranos-1-yl)-benzene | 1.5 | 1.5 | 1.5 | 1.5 | 1.5 | 1.5 |
| Propylene glycol | 50.0 | 50.0 | 50.0 | 50.0 | 50.0 | 50.0 |
| Glycerin | 0.0 | 32.5 | 32.7 | 26.8 | 52.1 | 46.6 |
| Ethanol abs. | — | — | — | 5.00 | — | 5.00 |
| Honey flavor | 0.15 | 0.15 | 0.15 | 0.15 | 0.15 | 0.15 |
| Propyl-hydroxy-benzoate | 0.20 | — | 0.20 | — | — | — |

TABLE 7-continued

| Ingredient | Trial 1 [g/100 mL] | Trial 2 [g/100 mL] | Trial 3 [g/100 mL] | Trial 4 [g/100 mL] | Trial 5 [g/100 mL] | Trial 6 [g/100 mL] |
|---|---|---|---|---|---|---|
| Phosphate buffer pH 6.8 | 52.2 | 20.0 | 20.0 | 20.0 | — | — |

After preparation of the samples, the solutions were filtrated via a 0.22 μm filter. The following microorganisms were tested: *Pseudomonas aeruginosa, Straphylococcus aureus, Escherichia coli, Candida albicans, Aspergillus brasiliensis, Zygosaccharomyces rouxi.*

In the performed tests the USP 34 Method <51> Criteria as listed in Table 6 were found to be fulfilled for all solutions for all microorganisms. It was also found, that an additional preservative like propyl-hydroxy-benzoate is not needed to get antimicrobial effectiveness.

Example 5

Formulation samples were produced as follows:
1) Preparation of a basic excipient solution consisting of an aqueous pH 6 phosphate buffer (21.05 mg/mL $KH_2PO_4$ and 8.82 mg/mL $Na_2HPO_4*12H_2O$) and 20% (m/v) propylene glycol
2) 1.34% (m/v) 1-cyano-2-(4-cyclopropyl-benzyl)-4-(β-D-glucopyranos-1-yl)-benzene*L-proline*$H_2O$ (corresponds to 1.0% 1-cyano-2-(4-cyclopropyl-benzyl)-4-(β-D-glucopyranos-1-yl)-benzene) were dissolved in the basic excipient solution (batch size: 2000 mL)
3) A solubilizing agent was weight into a 300 mL flask and filled up to the mark with the solution The following solubilizing agents were used:
Experiment 1: 0.1% (m/v) SDS
Experiment 2: 1% (m/v) Cremophor RH 40
Experiment 3: 1% (m/v) Lutrol F 68
Experiment 4 8% (m/v) PEG 300
For the experiments 1, 2, 3 and 4 no additional significant degradation are measured by HPLC analytics (table 8).

TABLE 8

| | Chemical by product/ degradation measured by HPLC | |
|---|---|---|
| Experiment | 3 months at 25° C./60% r.h. | 3 months at 40° C./75% r.h. |
| 1 | no | no |
| 2 | no | no |
| 3 | no | no |
| 4 | no | no |

Example 6

Formulation samples were produced as follows:
1) 1380 g propylene glycol and 619 g $H_2O$ were mixed in a 3000 mL beaker.
2) 7.1 g hydroxyl ethyl cellulose, as a viscosity-enhancing agent, was slowly added during intensive mixing with a propeller mixer.
3) The mixture was kept for 30 minutes for swelling.
4) The mixture was heated up to 70° C. during mixing and additionally mixed for further 10 minutes at 70° C.
5) The heater was switched off to cool down the mixture to room temperature during stirring.
6) 124.4 g NaOH 1N, 9.4 g citric acid monohydrate and 184 g ethanol absolute were added during stirring at room temperature until the solution is clear.
7) 46.1 g 1-cyano-2-(4-cyclopropyl-benzyl)-4-(β-D-glucopyranos-1-yl)-benzene*L-proline*$H_2O$ is added and stirred until the solution was clear.
8) The mixture (called stock-solution) was filtered under pressure with an 8 μm filter.

Trials with different flavors:
199.7 g stock-solution was filled in a separate beaker and 0.3 g of flavor was added (see table 9, experiments 2 to 7, experiment 1 is the stock solution).

Trials with different sweeteners:
199.98 g stock solution was filled in a separate beaker and 0.02 g of sweetener was added (see Table 9, experiments 8 and 9).

TABLE 9

| Experiment | Flavor/sweetener | pH-value | Turbidity [NTU] | Density [g/ml] |
|---|---|---|---|---|
| 1 | Stock solution | 7.1 | 1.8 | 1.029 |
| 2 | Honey flavor | 7.1 | 2.0 | 1.031 |
| 3 | Lime/Salvia flavor | 7.2 | 1.9 | 1.031 |
| 4 | Jasmine flavor | 7.1 | 1.8 | 1.031 |
| 5 | Lavender flavor | 7.2 | 1.9 | 1.031 |
| 6 | Peppermint flavor | 7.1 | 1.9 | 1.030 |
| 7 | Raspberry flavor | 7.0 | 1.8 | 1.030 |
| 8 | Saccharine | 7.1 | 1.8 | 1.030 |
| 9 | Aspartame | 7.1 | 1.8 | 1.032 |

For all depicted experiments the solutions are considered as clear (opalescent value <3 NTU, see Table 1).

REFERENCES (1) European Pharmacopoeia 7$^{th}$ edition, Method 5.1.3
(2) European Pharmacopoeia 8$^{th}$ edition, Chapter 2.2.1
(3) United States Pharmacopeia (USP) 34, Method <51>
(4) US 2014/031540
(5) WO 2007/028814
(6) WO 2007/080170
(7) WO 2007/093610
(8) WO 2007/128749
(9) WO 2008/144316
(10) WO 2013/079501
(11) WO 2014/016381
(12) WO 2014/195966
(13) WO 2015/110402
(14) Xu G et al., Journal of Medical Chemistry 2014, 57: 1236-1251

The invention claimed is:
1. An aqueous liquid pharmaceutical composition comprising at least one SGLT-2 inhibitor and one or more polar organic solvents, wherein the one or more polar organic solvents is selected from the group consisting of ethanol, propane-1,2-diol (propylene glycol), propane-1,2,3-triol (glycerol), and mixtures thereof, and the at least one SGLT-2 inhibitor comprises 1-cyano-2-(4-cyclopropyl-benzyl)-4-(μ-D-glucopyranos-1-yl)-benzene according to formula (I):

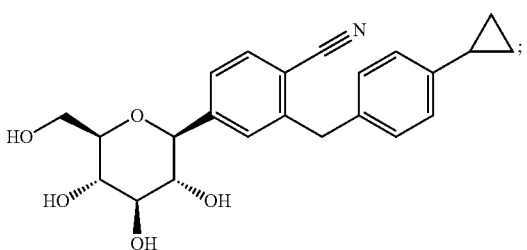

(I)

wherein each of the one or more polar organic solvents is provided in an amount such that the liquid pharmaceutical composition as a whole is characterized by a Log P-Parameter of less than zero and equal to or greater than −2.0.

2. The liquid pharmaceutical composition according to claim 1, wherein 1-cyano-2-(4-cyclopropyl-benzyl)-4-(β-D-glucopyranos-1-yl)-benzene is the only SGLT-2 inhibitor contained in such liquid pharmaceutical composition.

3. The liquid pharmaceutical composition according to claim 1, wherein said liquid pharmaceutical composition is suitable for direct administration to a mammal.

4. The liquid pharmaceutical composition according to claim 3, wherein the mammal is a horse, cat or dog.

5. The liquid pharmaceutical composition according to claim 3, wherein said liquid pharmaceutical composition is sterile.

6. The liquid pharmaceutical composition according to claim 1, wherein said liquid pharmaceutical composition is a solution, an emulsion or a suspension.

7. The liquid pharmaceutical composition according to claim 1, wherein the one or more polar organic solvents are independently from each other characterized by a negative $\log_{10}$ P value.

8. The liquid pharmaceutical composition according to claim 7, wherein said polar organic solvents are independently of each other characterized by a negative decadic logarithmic partition coefficient (P) in an n-octanol/water system according to formula (II):

$\log_{10} P_{n\text{-}octanol/water}$=concentration of unionized compound in $n$-octanol/concentration of unionized compound in water (II).

9. The liquid pharmaceutical composition according to claim 1, wherein said liquid pharmaceutical composition does not: (a) comprise ethanol as the one or more polar organic solvents; or (b) comprise only propane-1,2-diol (propylene glycol) as single polar organic solvent.

10. The liquid pharmaceutical composition according to claim 1, wherein said liquid pharmaceutical composition additionally comprises an aqueous buffer.

11. The liquid pharmaceutical composition according to claim 10, wherein said liquid pharmaceutical composition has a measured pH value of from 3 to 9.

12. The liquid pharmaceutical composition according to claim 1, wherein said liquid pharmaceutical composition additionally comprises one or more solubilizing agents, one or more viscosity-enhancing agents, or one or more flavors or sweeteners.

13. The liquid pharmaceutical composition according to claim 12, wherein said one or more solubilizing agents are selected from the group consisting of: surfactants, anionic surfactants, non-ionic surfactants, hydrogenated castor oils, polyoxyethylene-polyoxypropylene block copolymers, polyethylene glycols, propyleneglycol derivatives and mixtures thereof.

14. The liquid pharmaceutical composition according to claim 13, wherein said one or more solubilizing agents are selected from the group consisting of: Sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 300, propylenglycol monolaurate and mixtures thereof.

15. The liquid pharmaceutical composition according to claim 12, wherein said one or more viscosity-enhancing agents are selected from the group consisting of: inorganic gel forming agents, organic gel forming agents, cellulose derivatives, and mixtures thereof.

16. The liquid pharmaceutical composition according to claim 15, wherein said one or more viscosity-enhancing agents are selected from the group consisting of: hydroxyl ethyl cellulose, hydroxyl propyl methyl cellulose, silicon dioxide, and mixtures thereof.

17. The liquid pharmaceutical composition according to claim 12, wherein said one or more flavors or sweeteners are selected from the group consisting of: honey flavor, lime/salvia flavor, jasmine flavor, lavender flavor, peppermint flavor, raspberry flavor, lemon flavor, herbs flavor, saccharine, aspartame, and mixtures thereof.

18. The liquid pharmaceutical composition according to claim 1, wherein said liquid pharmaceutical composition does not comprise any apolar organic solvents, which are independently from each other characterized by a $\log_{10}$ P value of equal to or higher than 0.

19. The liquid pharmaceutical composition according to claim 1, wherein such liquid pharmaceutical composition is for oral or parenteral administration.

20. The liquid pharmaceutical composition according to claim 1, comprising:
(i) 0.5-5.0 g/100 mL (% w/w) 1-cyano-2-(4-cyclopropyl-benzyl)-4-(β-D-glucopyranos-1-yl)-benzene;
(ii) 10-60 g/100 mL (% w/w) propylene glycol;
(iii) 0-60 g/100 mL (% w/w) glycerol;
(iv) 0-20 g/100 mL (% w/w) ethanol;
(v) 0-1 g/100 mL (% w/w) flavor and/or sweetener;
(vi) 0-52 g/100 mL (% w/w) aqueous buffer;
(vii) 0-10 g/100 mL (% w/w) solubilizing agent; and
(viii) 0-5 g/100 mL (% w/w) viscosity-enhancing agent.

21. An aqueous liquid pharmaceutical composition comprising at least one SGLT-2 inhibitor and one or more polar organic solvents, wherein the one or more polar organic solvents is selected from the group consisting of ethanol, propane-1,2-diol (propylene glycol), propane-1,2,3-triol (glycerol), and mixtures thereof, and the at least one SGLT-2 inhibitor comprises 1-cyano-2-(4-cyclopropyl-benzyl)-4-(β-D-glucopyranos-1-yl)-benzene according to formula (I):

(I)

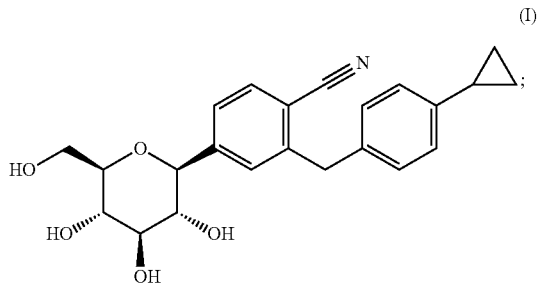 [SMILES: N#Cc1ccc([C@@H]2O[C@H](CO)[C@@H](O)[C@H](O)[C@H]2O)cc1Cc1ccc(C2CC2)cc1]

wherein each of the one or more polar organic solvents is provided in an amount such that the liquid pharmaceutical composition has a NTU (Nephelometric Turbidity Unit) value of equal to or less than 10.0.

22. The liquid pharmaceutical composition according to claim 21, wherein the liquid pharmaceutical composition has a NTU (Nephelometric Turbidity Unit) value of less than 3.0.

23. A kit-of-parts comprising:
(a) a liquid pharmaceutical composition according to claim 1; and
(b) a package leaflet including the information that the liquid pharmaceutical composition is to be used for the prevention or treatment of one or more medicinal indications in a subject in need of such prevention or treatment, which are selected from among the medicinal indications:
  (i) a metabolic disorder of an equine animal, wherein the metabolic disorder is selected from the group consisting of: insulin resistance, hyperinsulinemia, impaired glucose tolerance, dyslipidemia, dysadipokinemia, subclinical inflammation, systemic inflammation, low grade systemic inflammation, obesity, regional adiposity, and mixtures thereof;
  (ii) a metabolic disorder of an equine animal, wherein the metabolic disorder is selected from the group consisting of: laminitis, vascular dysfunction, hypertension, hepatic lipidosis, atherosclerosis, hyperadrenocorticism, Pituitary Pars Intermedia Dysfunction, Equine Metabolic Syndrome and mixtures thereof;
  (iii) a metabolic disorder of a feline animal, wherein the metabolic disorder is selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy, Syndrome X (metabolic syndrome), loss of pancreatic beta cell function and mixtures thereof;
  (iv) a metabolic disorder of a canine animal, wherein the metabolic disorder is selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction, musculoskeletal disorders, Syndrome X (metabolic syndrome), and mixtures thereof.

24. A process for producing the liquid pharmaceutical composition according to claim 1, comprising the steps:
  (i) mixing the one or more polar organic solvents to form a mixture;
  (ii) adding water to the mixture; and
  (iii) dissolving 1-cyano-2-(4-cyclopropyl-benzyl)-4-(β-D-glucopyranos-1-yl)-benzene in the mixture resulting from step (i) or step (ii).

25. The process for producing the liquid pharmaceutical composition according to claim 24, further comprising dissolving further excipients in the mixture resulting from step (iii).

26. The process for producing the liquid pharmaceutical composition according to claim 24, further comprising filtrating the mixture resulting from step (iii).

27. The process for producing the liquid pharmaceutical composition according to claim 24, further comprising an additional mixing step is performed after each step.

28. A method for treating medicinal indications in a mammal in need of such treatment comprising administering to the mammal the liquid pharmaceutical composition of claim 1, wherein the treating medicinal indications is selected from the group consisting of:
  (i) a metabolic disorder of an equine animal, wherein the metabolic disorder is selected from the group consisting of: insulin resistance, hyperinsulinemia, impaired glucose tolerance, dyslipidemia, dysadipokinemia, subclinical inflammation, systemic inflammation, low grade systemic inflammation, obesity, regional adiposity, and mixtures thereof;
  (ii) a metabolic disorder of an equine animal, wherein the metabolic disorder is selected from the group consisting of: laminitis, vascular dysfunction, hypertension, hepatic lipidosis, atherosclerosis, hyperadrenocorticism, Pituitary Pars Intermedia Dysfunction, Equine Metabolic Syndrome and mixtures thereof;
  (iii) a metabolic disorder of a feline animal, wherein the metabolic disorder is selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy, Syndrome X (metabolic syndrome), loss of pancreatic beta cell function and mixtures thereof;
  (iv) a metabolic disorder of a canine animal, wherein the metabolic disorder is selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction, musculoskeletal disorders, Syndrome X (metabolic syndrome), and mixtures thereof.

\* \* \* \* \*